United States Patent [19]

van Dijk et al.

[11] Patent Number: 4,508,652

[45] Date of Patent: Apr. 2, 1985

[54] PROCESS FOR THE TRIMERIZATION OF UNSATURATED FATTY ACIDS

[75] Inventors: Jacob van Dijk, Maassluis; Johannes W. Renken, Gouda; Jan G. Dekker, Rozenburg; Johannes Helmond, Gouda, all of Netherlands

[73] Assignee: National Distillers and Chemical Corporation, New York, N.Y.

[21] Appl. No.: 391,258

[22] Filed: Jun. 23, 1982

[30] Foreign Application Priority Data

Jun. 25, 1981 [NL] Netherlands .................. 8103066

[51] Int. Cl.$^3$ .......................... C08H 3/00; C08H 5/00
[52] U.S. Cl. .................................................. 260/407
[58] Field of Search ........................................ 260/407

[56] References Cited

U.S. PATENT DOCUMENTS

| 2,435,619 | 2/1948 | Young | 260/407 |
| 2,516,590 | 7/1950 | Pratt | 260/407 |
| 2,746,942 | 5/1956 | Sample et al. | 260/407 |
| 2,794,017 | 5/1957 | Palmer et al. | 260/407 X |
| 3,367,952 | 2/1968 | Arlt | 260/407 |
| 3,371,070 | 2/1968 | Chang et al. | 260/407 X |
| 3,393,214 | 7/1968 | Parker et al. | 260/407 |
| 3,441,577 | 4/1969 | Baltes et al. | 260/407 |
| 3,661,956 | 5/1972 | Silverstone | 260/407 |
| 4,367,151 | 1/1983 | Kinsman et al. | 260/407 X |

FOREIGN PATENT DOCUMENTS

| 2125848 | 12/1971 | Fed. Rep. of Germany | 260/407 |
| 321725 | 11/1929 | United Kingdom | 260/407 |
| 341453 | 1/1931 | United Kingdom | 260/407 |

Primary Examiner—Helen M. S. Sneed
Attorney, Agent, or Firm—Kenneth D. Tremain; Gerald A. Baracka

[57] ABSTRACT

A process is provided whereby high trimer content products are obtained by the polymerization of unsaturated fatty acids or lower alkyl esters thereof. The process entails heating the fatty acid/ester material at a temperature of at least 120° C. in the presence of a sulphonic acid catalyst which is dissolved therein.

9 Claims, No Drawings

PROCESS FOR THE TRIMERIZATION OF UNSATURATED FATTY ACIDS

BACKGROUND OF THE INVENTION

For certain applications there is need of polymeric fatty acids which consist completely or for the greater part of trimer and it is therefore attractive to have available a method of preparation which provides high yields of polymeric fatty acid and in which, moreover, the polymeric fraction has a high content of trimer.

From the U.S. Pat. No. 3,097,220 it is already known to prepare polymeric fatty acids having a content of trimer (50–60% trimer), by carrying out the reaction in two steps, namely: in a first step by heating with a Friedel-Crafts catalyst ($BF_3$) and thereafter in a second step by heating in the presence of water and a clay catalyst. The use of the gaseous, toxic $BF_3$ gives problems, because the fatty acid/$BF_3$ mixture is extremely corrosive and requires special reactors (e.g. coated with Teflon). Moreover, the removal of that catalyst is difficult and the catalyst cannot be recovered.

On the other hand it is already known from the Dutch patent application No. 7312712 (=German DOS No. 22 50 470) to dimerize unsaturated fatty acids with the aid of ion-exchange resins which are insoluble therein and which contain sulphonic acid groups. According to said patent application, page 4, lines 23–29, the reaction product thus obtained consists mainly of dimeric fatty acids and only for 10–20% by weight of trimeric and higher polymeric products. Moreover, the yield of polymeric fatty acids is relatively low.

U.S. Pat. No. 3,367,952 describes a similar process, though without indicating what the yields of dimer and trimer are. In our experience this process also yields a relatively small amount of trimer.

SUMMARY OF THE INVENTION

According to the present process unsaturated fatty acids or $C_{1-4}$ alkyl esters thereof are polymerized to obtain high trimer content products, typically consisting of 60–75% by weight trimer and higher oligomers. For the process of this invention the unsaturated fatty acid (ester), preferably having a high linoleic acid (ester) content, is reacted at a temperature of at least 120° C. in the presence of from about 0.5 to 20% by weight sulfonic acid catalyst, based on the fatty acid (ester). Especially useful sulfonic acid catalysts for the process include methanesulfonic acid and p-toluenesulfonic acid.

DETAILED DESCRIPTION

The invention relates to a process for the trimerization of unsaturated fatty materials such as fatty acids and their lower alkyl esters (i.e. monocarboxylic acids), which fatty acids contain one or more double bonds. These fatty acids can contain 14–22 carbon atoms and in the case of multiple double bonds the unsaturation can be conjugated or random. As a rule, natural $C_{18}$ fatty acids are used which contain oleic acid and especially linoleic acid and linolenic acid. Preferred are fatty acid mixtures and their esters which contain at least 25%, and more preferably at least 35%, of a tri- or higher unsaturated fatty acid, such as linolenic acid, linseed oil fatty acids, or similar fatty acid mixtures which have been obtained by mixing of fatty acids. The reaction products thus obtained usually show relatively low ester contents. It is preferred to trimerize free fatty acids, but satisfactory results can be obtained when the $C_1$-$C_4$ alkyl esters are polymerized.

By trimerization is here understood the preparation—starting from fatty acids—of reaction mixtures which contain especially tricarboxylic acids ($C_{54}$ as a rule) having a molecular weight approximately three times that of the starting fatty acid. According to the present invention, reaction mixtures are obtained which contain, in addition to unpolymerized monocarboxylic acids which are distilled off, a polymeric (residue) fraction, which fraction consists for approximately 50 to 85% by weight of trimer and possibly higher oligomers and of which the remainder is dimer.

According to the present process, the unsaturated fatty acid is now trimerized at a temperature of at least 120° C. for several hours in the presence of a sulphonic acid catalyst which is dissolved in the fatty acid. This reaction can, for example, be carried out in a simple enamelled reactor. In doing so, the reaction time is kept dependent on the reaction temperature and the amount of catalyst, this in order to convert the initially forming ester dimer and ester trimer further. At a temperature of 140° C., in a few hours with an amount of methanesulfonic acid catalyst of about 4%, good conversions into trimer with relatively low contents of ester groups are obtained.

Generally the amount of sulphonic acid catalyst is between 0.5 and 20% by weight, and more preferably 1.0 to 10% by weight, based on the unsaturated fatty acid. Useful sulphonic acids are soluble in fatty acid/ester under the reaction conditions and are preferably monosulphonic or disulphonic acids, more particularly aliphatic or aromatic sulphonic acids. Suitable sulphonic acids are e.g. methanesulphonic acid, halogenated methanesulphonic acids such as trifluoromethanesulphonic acid, benzenesulphonic acid, p-toluenesulphonic acid, xylenesulphonic acid, naphthalenesulphonic acid, naphthalenedisulphonic acid, e.g. dinonylnaphthalenedisulphonic acid. Monosulphonic acids like methanesulphonic acid and p-toluenesulphonic acid are preferred. The sulphonic acid catalyst used according to the present invention can be recovered and reused.

In order to obtain a high yield of trimer together with a satisfactory low ester value it is desirable that the starting material has a sizable content of linolenic acid. At least 25% linolenic acid, preferably at least 35% linolenic acid, is desired. Linseed oil fatty acids are therefore a particularly suitable starting material.

It may be desirable, particularly if the trimerization is carried out above 180° C., that this be carried out under pressure, e.g. in an inert atmosphere.

The reaction is continued up to the point that the ester value of the final product (difference between saponification value and acid value) is low, namely below 35, preferably below 20.

After termination of the reaction, the sulphonic acid is removed, e.g. washed out (and possibly recirculated) and the monomer is distilled off, whereafter a polymeric fraction remains which, when the process is well carried out, amounts to 50 to 70% by weight of the starting material and which product consists of 60 to 75% by weight of trimer and higher oligomers (determined with GLC), so that, according to the present invention, conversions into trimer of about 50% can be obtained.

The invention will now be further explained with the help of the following examples.

EXAMPLES 1-5

Linseed oil fatty acids (content of linolenic acid 50%) were heated in a glass reactor with 7% p-toluenesulphonic acid under nitrogen. After termination, the sulphonic acid was washed out, the polymer dried and monomer distilled off. The results are given in the following table.

| Example | Reaction Time (h) | Temperature (°C.) | Yield (wt. %) | Acid Value | D/T* (GLC) |
|---|---|---|---|---|---|
| 1 | 4 | 160 | 60 | 148 | 33/67 |
| 2 | 4 | 175 | 61 | 170 | 30/70 |
| 3 | 6 | 160 | 57 | 168 | 31/69 |
| 4 | 6 | 175 | 57 | 172 | 29/71 |
| 5 | 4 | 185/200 | 54 | 178 | 36/64** |

*Dimer:Trimer ratio
**autoclave 1-3.5 atm.

EXAMPLES 6-9

Linseed oil fatty acids (having a linolenic acid content of 45%) were trimerized for 4 hours in the presence of 3.5% by weight of methanesulfonic acid (Example 9: 2% by weight). The results are given in the following table.

| Example | Reaction Temp. °C. | Yield (wt. %) | Acid Value | D/T (GLC) |
|---|---|---|---|---|
| 6 | 150 | 59 | 167 | 30/70 |
| 7 | 175 | 58 | 183 | 28/72 |
| 8 | 200 | 58 | 171 | — |
| 9 | 175 | 55 | 173 | 26/74 |

EXAMPLE 10

Linseed oil fatty acids (containing 50% linolenic acid) were trimerized for 4 hours in the presence of 7% by weight of p-toluenesulphonic acid at 175° C., a yield of 64% by weight of residue being obtained (acid value 170; saponification value 190). The first washing water of the trimerized reaction product, which contained the greatest part of the p-tolunensulphonic acid, was thereafter added to a second portion of linseed oil fatty acids, which was subsequently also trimerized for 4 hours at 175° C. Here a yield of 63% trimer was obtained, of which the acid value was 170 and the saponification value 194.

EXAMPLES 11-13

In a manner analogous to that of Example 10, trimerization was carried out with 9.25% 5-sulphosalicyclic acid, 5.8% benzenesulphonic acid and 8.1% xylenesulphonic acid, yields of residue being obtained of 52, 54 and 50%, respectively. The percentages of trimer in the residue were 81, 84 and 83%, respectively.

EXAMPLES 14-15

In these Examples lower alkyl esters of linseed fatty acids were trimerized. The linseed fatty acids contained 45% of linolenic acid. The procedure followed has been outlined in Example 10. The results are tabulated below:

| Feed stock | Type cat. | Cat. conc. | Temp. (°C.) | Time (h) | Yield (wt. %) | A.V. (res.) |
|---|---|---|---|---|---|---|
| methyl-esters | p-TSA | 7 | 175 | 6 | 53.0 | 28 |
| ethyl-esters | MSA | 3.5 | 175 | 4 | 50.5 | 17 |

TSA = p-toluenesulphonic acid
MSA = methanesulphonic acid

EXAMPLES 16-17

These examples illustrate the effect of the content of the triunsaturation upon yield and properties. The procedure followed has been outlined in Example 10.

| Feed stock | Type cat. | Cat. conc. | Temp. (°C.) | Time (h) | Yield (wt. %) | A.V. (res.) | D/T |
|---|---|---|---|---|---|---|---|
| Soya Fatty Acids (8% linolenic acid) | MSA | 3.5 | 175 | 6 | 44 | 153 | 21/79 |
| Soya + linseed f.a. (50:50) | MSA | 3.5 | 175 | 6 | 50 | 158 | 25/75 |

We claim:

1. A process for the polymerization of $C_{14-22}$ unsaturated fatty acids and $C_{1-4}$ alkyl esters thereof which comprises dissolving 0.5 to 20% by weight of an aliphatic or aromatic monosulfonic acid catalyst in said unsaturated fatty acid/ester and heating at a temperature of at least 120° C.

2. The process according to claim 1 wherein the amount of sulphonic acid is 1.0-10% by weight, based on the fatty acid/ester.

3. The process according to claim 2 wherein the sulphonic acid is p-toluenesulphonic acid.

4. The process according to claim 2 wherein the sulphonic acid is methanesulfonic acid.

5. The process according to claims 1, 2, 3 or 4 wherein the fatty acid/ester is derived from a fatty material containing at least 25% linolenic acid.

6. The process of claim 5 wherein the fatty acid/ester is derived from a fatty material containing at least 35% linolenic acid.

7. The process of claim 6 wherein the linseed oil fatty acids are polymerized.

8. The process of claim 7 wherein the temperature is in the range 150° to 300° C.

9. The process of claim 8 wherein the polymerization is carried out under increased pressure.

* * * * *